US006100092A

United States Patent [19]

Borysyuk et al.

[11] Patent Number: 6,100,092

[45] Date of Patent: Aug. 8, 2000

[54] MATERIALS AND METHODS FOR AMPLIFYING POLYNUCLEOTIDES IN PLANTS

[75] Inventors: Mykola Borysyuk; Lyudmyla Borysyuk, both of East Brunswick; Ilya Raskin, Manalapan, all of N.J.

[73] Assignee: Board of Trustees, Rutgers The State University of New Jersey, New Brunswick, N.J.

[21] Appl. No.: 09/097,541

[22] Filed: Jun. 15, 1998

[51] Int. Cl.[7] ............................ C12N 5/04; C12N 15/29; C12N 15/69; C12N 15/90; C12N 15/82

[52] U.S. Cl. ........................ 435/468; 435/69.1; 435/91.1; 435/320.1; 435/411; 435/414; 435/417; 435/419; 800/278; 800/288; 800/298; 800/317.2; 800/317.3; 800/317.4; 536/23.6

[58] Field of Search ............................... 435/69.1, 320.1, 435/410, 411, 414, 417, 419, 468, 91.1; 536/23.6; 800/278, 295, 298, 317, 317.2, 317.3, 317.4, 288

[56] References Cited

U.S. PATENT DOCUMENTS

| 5,106,739 | 4/1992 | Comai et al. | 435/468 |
|---|---|---|---|

FOREIGN PATENT DOCUMENTS

| 1695/96 | 9/1996 | Austria | C12N 15/82 |
|---|---|---|---|
| 0 243 553 | 11/1987 | European Pat. Off. | C12N 15/00 |
| WO 84/02920 | 8/1984 | WIPO | C12N 15/00 |
| WO 96/04392 | 2/1996 | WIPO | C12N 15/82 |
| WO 98/13505 | 8/1996 | WIPO | C12N 15/82 |

OTHER PUBLICATIONS

Gruendler et al, J. Mol. Biol., vol. 221, pp. 1209–1222, 1991.

Borisjuk et al, Plant Mol. Biol., vol. 35, pp. 655–660, 1997.

Perry et al, Mol. Gen. Genet., vol. 221, pp. 102–112, 1990.

Borisjuk et al, Plant Mol. Biol., vol. 21, pp. 381–384, 1993.

Hernandes et al, EMBO J., vol. 12, pp. 1475–1485, 1993.

Odell et al, Mol. Gen. Genet., vol. 223, pp. 369–378, 1990.

Borisjuk, N.V. et al., "Novel class of rDNA repeat units in somatic hybrids between Nicotiana and Atropa," Theor. Appl. Genet., 76:108–112 (1988).

Borisjuk, N.V. et al., "Structural analysis of rDNA in the genus Nicotiania," Plant Molecular Biology, 35:655–660 (1997).

Christou, P., "Strategies for variety–independent genetic transformation of important cereals, legumes and woody species utilizing particle bombardment," Euphytica, 85:13–27 (1995).

Doelling, J.H. et al., "Functional analysis of *Arabidopsis thaliana* rRNA gene and spacer promoters in vivo and by transient expression," Proc. Natl. Acad. Sci. USA, 90:7528–7532 (Aug. 1993).

Doelling, J.H. et al., "The minimal ribosomal RNA gene promoter of *Arabidopsis thaliana* includes a critical element at the transcription initiation site," The Plant Journal, 8(5):683–692 (1995).

Fan, H. et al., "In vitro transcription of plant RNA polymerase I–dependent rRNA genes is species–specific," The Plant Journal, 8(2):295–298 (1995).

Gruendler, P. et al., "rDNA Intergenic Region from *Arabidopsis thaliana*: Structural Analysis, Intraspecific Variation and Functional Implications," J. Mol. Biol., 221:1209–1222 (1991).

Hemann, C. et al., "High–Copy Expression Vector–Based on Amplification–Promoting Sequences," DNA and Cell Biology, 13(4):437–445 (1994).

Holst, A. et al., "Murine Genomic DNA Sequences Replicating Autonomously in Mouse L Cells," Cell, 52:355–365 (1988).

Hood, E.E. et al., "The Hypervirulence of *Agrobacterium tumefaciens* A281 Is Encoded in a Region of pTiBo542 Outside of T–DNA," J. Bacteriol., 168(3): 1291–1301 (1986).

Jackson, S.D. et al., "Protein–binding to reiterated motifs within the wheat rRNA gene promoter and upstream repeats," Plant Molecular Biology, 20:911–919 (1992).

Jähne, A. et al., "Genetic engineering of cereal crop plants: a review," Euphytica, 85:35–44 (1995).

Kellems, R.E., "Gene Amplification Strategies for Protein Production in Mammalian Cells," Methods in Molecular Genetics, 5:143–155 (1994).

Lopes, T.S. et al., "High–copy–number integration into the ribosomal DNA of *Saccharomyces cerevisiae*: a new vector for high–level expression," Gene, 79:199–206 (1989).

Marilley, M. et al., "Common DNA structural features exhibited by eukaryotic ribosomal gene promoters," Nucleic Acids Research, 24(12):2204–2211 (1996).

Meyer, J. et al., "Inhibition of HIV–1 replication by a high–copy–number vector expressing antisense RNA for reverse transcriptase," Gene, 129:263–268 (1993).

Reichel, C. et al., "Enhanced green fluorescence by the expression of an *Aequorea victoria* green fluorescent protein mutant in mono–and dicotyledonous plant cells," Proc. Natl. Acad. Sci.(USA), 93:5888–5893 (1996).

(List continued on next page.)

*Primary Examiner*—David T. Fox
*Assistant Examiner*—Ashwin D. Mehta
*Attorney, Agent, or Firm*—Marshall, O'Toole, Gerstein, Murray & Borun

[57] ABSTRACT

Products and methods for amplifying target nucleic acids using cells derived from plants are disclosed. The products include nucleic acids containing a plant active Amplification Promoting Sequence (APS) and the methods exploit these products in amplifying target nucleic acids. Also disclosed are methods for amplifying target nucleic acids that express an encoded product, and the recovery of that expression product. The methods of the invention minimize operator intervention and exploit solar energy and the minimal nutrient needs of photoautotrophic organisms to provide inexpensive and indefinitely sustainable methods for producing a variety of amplified target nucleic acids and encoded products such as polypeptides.

14 Claims, 2 Drawing Sheets

OTHER PUBLICATIONS

Sambrook et al., §§9.47–9.51 in Molecular Cloning: A Laboratory Manual, (Cold Spring Harbor Laboratory Press, Cold Spring Harbor, New York 1989).

Vain, P. et al., "Foreign Gene Delivery Into Monocotyledonous Species," Biotechnology Advances, 13(4): 653–671 (1995).

Wegner, M. et al., "Cis–acting sequences from mouse rDNA promote plasmid DNA amplification and persistence in mouse cells: implication of HMG–I in their function," Nucleic Acids Research, 17(23):9909–9932 (1989).

Zastrow, G. et al., "Distinct mouse DNA sequences enable establishment and persistence of plasmid DNA polymers in mouse cells," Nucleic Acids Research, 17(5):1867–1879 (1989).

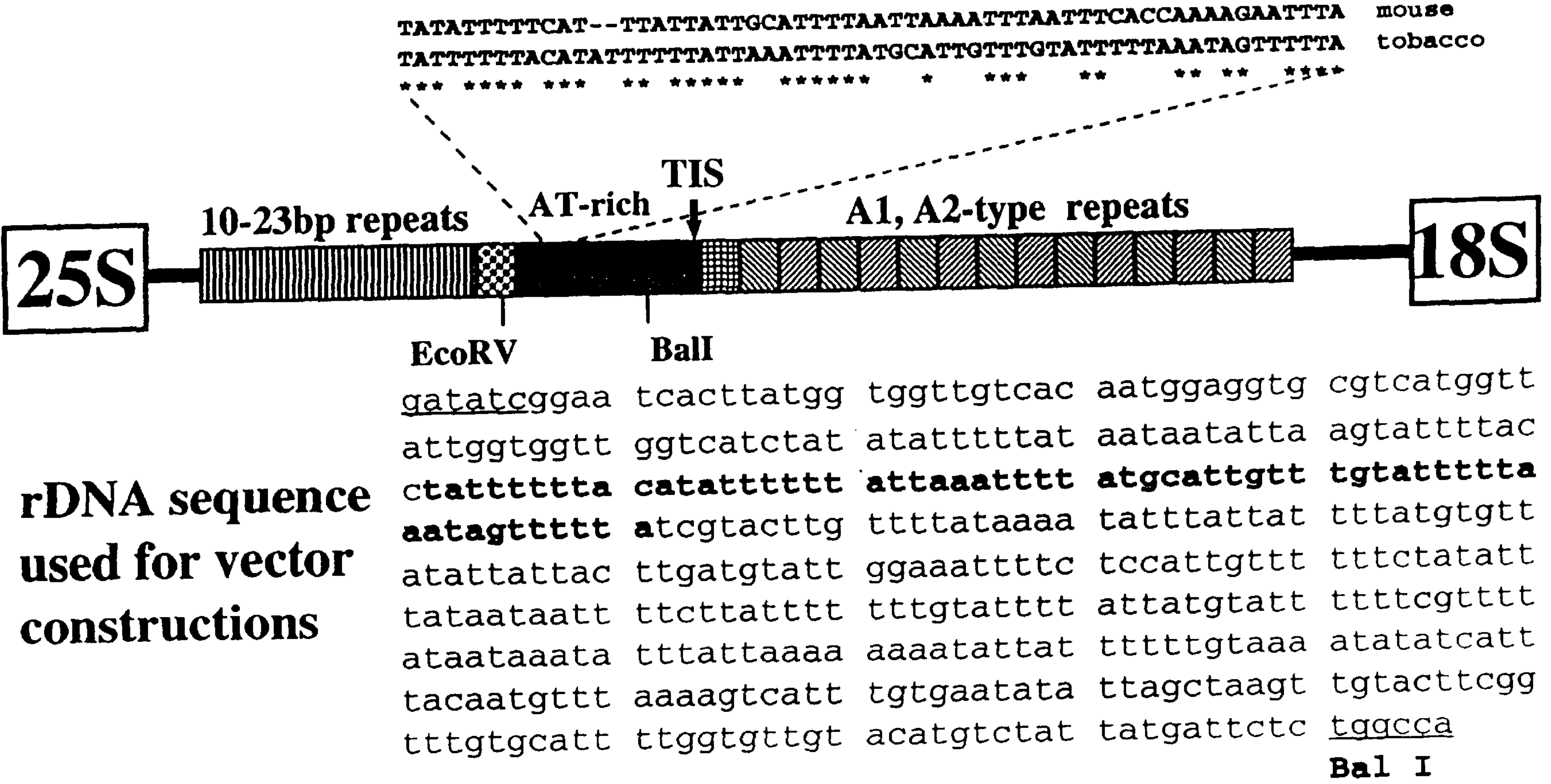
Fig. 1
TATATTTTTCAT--TTATTATTGCATTTTAATTAAAATTTAATTTCACCAAAAGAATTTA mouse
TATTTTTTACATATTTTTTATTAAATTTTATGCATTGTTTGTATTTTTAAATAGTTTTTA tobacco
*  *  * **** * *    ****
25S
10-23bp repeats
AT-rich
TIS
A1, A2-type repeats
18S
EcoRV
BalI
rDNA sequence used for vector constructions
gatatcggaa tcacttatgg tggttgtcac aatggaggtg cgtcatggtt
attggtggtt ggtcatctat atatttttat aataatatta agtattttac
ctattttttta catatttttt attaaatttt atgcattgtt tgtattttta
aatagttttt atcgtacttg ttttataaaa tatttattat tttatgtgtt
atattattac ttgatgtatt ggaaatttc tccattgttt tttctatatt
tataataatt ttcttatttt tttgtatttt attatgtatt ttttcgtttt
ataataaata tttattaaaa aaaatattat tttttgtaaa atatatcatt
tacaatgttt aaaagtcatt tgtgaatata ttagctaagt tgtacttcgg
tttgtgcatt ttggtgttgt acatgtctat tatgattctc tggcca
Bal I

MATERIALS AND METHODS FOR AMPLIFYING POLYNUCLEOTIDES IN PLANTS

FIELD OF THE INVENTION

The present invention relates to products and processes for amplification of nucleic acids and production of polypeptides in plants.

BACKGROUND

Biomolecules such as complex proteins and nucleic acids have shown their value as products in such diverse fields as medical diagnostics/therapeutics and agriculture. Given the potential value of the products, it is not surprising that the efficient large-scale production of these biomolecules remains an active area of inquiry in biotechnology. Existing methods vary in their capacities to produce a desired biomolecule and these methods vary in terms of the costs required to achieve those levels of production. Production methods exhibiting lowered per unit production costs would provide improved approaches to the generation of biomolecules.

One strategy for improving biomolecule production is directed to maximizing the yield of the desired biomolecule. One type of approach to maximizing yield has focused on minimizing the loss of biomolecules in the production process. Recovery of active biomolecules such as polypeptides is frequently lowered due to chemical events (e.g., oxidation) and biochemical events (e.g., nuclease- or protease-mediated degradation). Thus, some production methods address these losses by adding, e.g., an anti-oxidant (β-mercaptoethanol or dithiothreitol) or an inhibitor of either nucleases (e.g., vanadium complexes) or proteases (e.g., phenylmethylsulfonylfluoride). Alternative approaches modify the expressed biomolecule to confer increased stability (e.g., alkylation). However, all of these interventions are costly.

Other strategies to lower unit costs have concentrated on improving the gross yield of a desired biomolecule. Towards that end, refinements to production methods have been developed that increase the raw production of, e.g., a polypeptide by improving the genetic expression of the desired product. For example, a variety of recombinant techniques have been used to operatively link a coding region for a desired polypeptide to a strong (i.e., active) expression control signal such as a promoter An alternative approach exploits the copy number effect by amplifying copies of a coding region to provide more "substrate" for expression. For example, Schimke et al., J. Biol. Chem. 263:5989–5992 (1988), disclosed a technique that involved a recombinant construct that linked the Dihydrofolate Reductase (DHFR) gene to a coding region of interest. Because DHFR quantity is positively correlated to resistance to the anti-cancer drug methotrexate, challenging cells containing the construct with methotrexate selected for cells that had amplified the construct, thereby producing more DHFR and more of the desired expression product.

Another strategy for amplification has been the development of transformation systems that result in multiple copies of an introduced DNA sequence integrating into a host genome. The ribosomal DNA (i.e., rDNA) locus is an attractive target for integration since it provides a promisingly high number of target sites for integration, extending upwards from approximately 100 copies in eukaryotes. Lopes et al., Gene 79:199–206 (1989). Some multiple copy transformation systems targeting rDNA have been established using unicellular eukaryotes (Tondravi et al., Proc. Natl. Acad. Sci. (USA) 83:4369–4373 (1986); Lopes et al., (1989); Tsuge et al., Gene 90:207–214 (1990)) and cultured mouse fibroblasts (Hemann et al., DNA and Cell Biol. 13:437–445 (1994). Plasmid vectors containing sequences homologous to an rDNA region dramatically increased the transformation efficiency of the yeast *S. cerevisiae* and the phytopathogenic fungus *Alternaria alternata*. Yeast cells transformed with an rDNA-based expression vector containing the homologous gene for phosphoglycerate kinase (PGK) and a heterologous gene for thaumatin were shown to carry 100–200 copies of the introduced sequences per cell. Lopes et al., (1989). Under optimized conditions, the level of PGK in transformed cells was about 50% of total soluble protein. The yield of thaumatin in transformants exceeded by a factor of 100 the level of thaumatin observed in transformants carrying only a single thaumatin gene.

Hemann et al., (1994) extended this approach by developing a versatile high-copy expression system for mouse L fibroblasts, thereby overcoming a variety of biochemical deficiencies in enzyme-deficient cell lines. The system relied on the inclusion of an amplification promoting sequence (muNTS1), derived from the nontranscribed spacer region of murine rDNA, in the transformation vector. Wegner et al., Nucl. Acids Res. 17:9909–9932 (1989). The muNTS1 was originally isolated from mouse rDNA by screening with a vector containing a truncated promoter driving the expression of a thymidine kinase gene. The high copy number amplification was achieved by the 370-bp amplification promoting element (muNTS1). Holst et al., Cell 52:355–365 (1988). Under these conditions, muNTS1 promoted amplification of the integrated vector. Copy number determination showed that muNTS1 mediated a 40- to 800-fold amplification of the vector DNA in transfected L cells. Wegner et al. (1989). The high copy number resulted in increased expression levels of the reporter gene. Further, muNTS1 was reported to promote vector amplification without selective pressure for amplification. Meyer et al., Gene 129:261–268 (1993).

These approaches to biomolecule production have been implemented using host cells of fungal or animal origin. Frequently, a commercially desirable biomolecule is a eukaryotic (e.g., human) polypeptide requiring post-translational modifications such as glycosylation, phosphorylation, etc., that a yeast host cell cannot provide. The vast majority of the unmodified analogs of these desirable polypeptides lack activity and are of little commercial value. In contrast, animal cells are eukaryotic cells typically capable of properly modifying an expressed polypeptide such as a human polypeptide. Animal cells are heterotrophic cells, however, requiring the costly inputs of energy and nutrients. Additionally, animal cell and tissue cultures require the costly maintenance of sterile conditions to prevent destructive contamination. With respect to transgenic animals, sterile conditions may not need to be maintained but, in addition to ethical concerns, the use of transgenic animals as polypeptide factories requires the costly raising of the animals and the costly isolation of the desired biomolecule.

Therefore, a need continues to exist in the art for biomolecule production methods that optimize biomolecule yield and take advantage of the cost efficiencies inhering in the use of plant materials.

SUMMARY OF THE INVENTION

The products and methods of the present invention satisfy the aforementioned need in the art by providing a radically different approach to the production of biomolecules which relies on plant cells that have a biology far removed from either animal, fungal or bacterial cells. Plant cells are photoautotrophic cells which typically do not require an energy input. Moreover, plant cells typically require a minimal nutrient input in terms of number, quantity and cost. Thus, plant cells provide cost advantages over the more familiar animal, fungal and bacterial host cell environments. The products and methods of the invention are designed to amplify nucleic acids in the cells of a plant. The invention realizes the advantage of lowered costs resulting from reduced host cell requirements for energy and nutrients.

The present invention provides novel plant polynucleotides specifying Amplification Promoting Sequences (APSs) which are active in plants to amplify an adjacent target nucleic acid. Preferred APSs of the invention comprise A-T rich (preferably 80% or more) rDNA intergenic polynucleotide sequences derived from (or based on) e.g., sequences of *N. tabacum, L. esculentum* and *S. tuberosum*. Presently most preferred plant APSs comprise the *N. tabacum*-derived polynucleotide set out in SEQ ID NO:1 and plant polynucleotides which hybridize under stringent conditions to the complement of the sequence set forth in SEQ ID NO:1.

Also provided by the present invention are nucleotide segments comprising a plant APS and an adjacent target nucleic acid to be amplified, preferably located within the segment within 3000 nucleotides from the APS. Novel nucleotide segments of the invention may also comprise a plant APS and a homologous recombination locator polynucleotide functional to provide for site specific insertion of the APS within another polynucleotide, e.g., a plant host chromosome or vector. Preferred novel nucleotide segments comprise vectors, including Agrobacterium-derived plant transformation vectors.

In another aspect of the invention plants and plant host cells are provided which are stably transformed or transfected with plant-derived and non-plant derived APSs functional to amplify adjacent nucleic acids within the plants or plant cells. Such adjacent nucleic acids may be coding sequences (e.g., RNA and/or protein coding) or may be expression regulatory sequences. The present invention correspondingly provides novel methods for amplifying target nucleic acids within plants, which methods optionally include isolation of products coded thereby.

Numerous other aspects and advantages of the present invention will be apparent upon consideration of the following detailed description, including the drawing.

BRIEF DESCRIPTION OF THE DRAWING

FIG. 1 provides a graphic representation of the intergenic region separating 25S and 18S rDNAs of *N. tabacum*. Specifically illustrated are the 446 nucleotides (SEQ ID NO: 1) spanning the intergenic region between EcoRV and BalI restriction sites along a subsequence (nucleotides 102 through 161 of SEQ ID NO: 1) compared to nucleotides 50 through 107 of *M. musculus* rDNA muNTS1 sequence set out in Genbank Accession No. X52413; Wegner et al., Nucl. Acids Res. 17:9909–9932 (1989).

DETAILED DESCRIPTION

Figure 2:
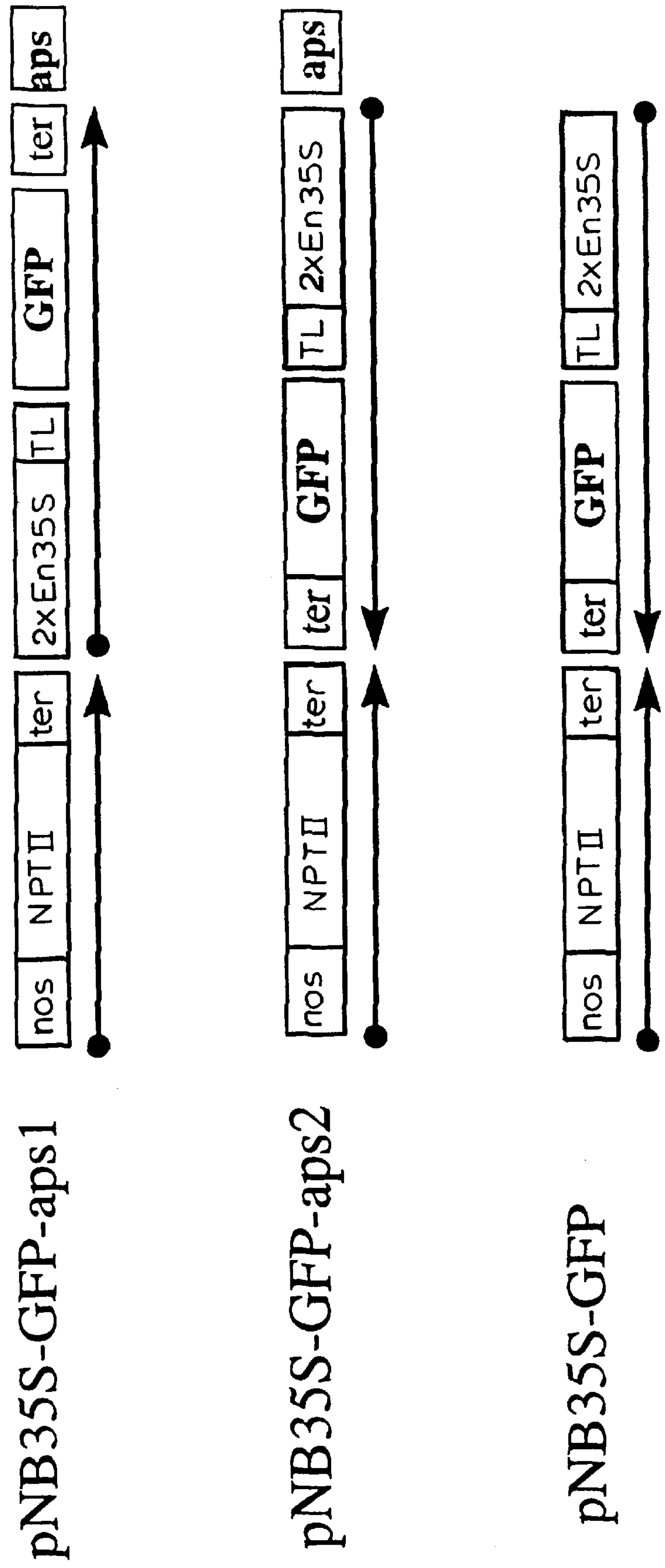
FIG. 2 graphically illustrates expression cassette components of illustrative plasmids pNB35S-GFP-aps1 and pNB35S-GFP-aps2 according to the invention, together with experimental control plasmid pNB35S-GFP. Abbreviations: nos—nopaline synthase promoter; NPT II—neomycin phosphotransferase gene conferring resistance to the antibiotic kanamycin; ter—nos terminator; 2×En 35S—the Cauliflower Mosaic Virus 35S promoter with two enhancers; the TEV 5' nontranslated sequence (TL); GFP—Green Fluorescent Protein; and aps—amplification promoting sequence.

The products and methods of the invention provide the tools to increase the copy number of target nucleic acids in plant cells, thereby improving the expression of valuable biomolecules such as RNAs and proteins. The following examples illustrate presently preferred embodiments of the invention. Example 1 describes the construction of recombinant polynucleotides for expression of Green Fluorescent Protein (GFP) in plants. Example 2 discloses the generation of transgenic plants by transformation with the recombinant polynucleotides of Example 1. Example 3 describes Southern, Northern, and protein expression analyses of samples from transgenic plants according to Example 2.

EXAMPLE 1

Plasmids were constructed using standard recombinant DNA techniques. Sambrook et al., in *Molecular Cloning*, Cold Spring Harbor Laboratory Press, Cold Spring Harbor, N.Y. (1989). Two recombinant molecules according to the invention are pNB35S-GFP-aps1 and pNB35S-GFP-aps2. These recombinant molecules were independently derived from plasmid Nt4-19. Nt4-19, in turn, is a subclone of Nt-4, which contains the whole sequence of the tobacco ribosomal DNA, or rDNA, intergenic spacer (Borisjuk et al., Plant Mol. Biol. 35:655–660 1997). To create Nt4-19, an EcoRV-HindIII fragment of the tobacco IGS sequence available from GenBank under Accession No. Y08422, containing the central AT-rich region of a tobacco intergenic space or IGS (including the transcription initiation site, TIS), was excised from Nt-4 and inserted into the SmaI and HindIII sites of plasmid pUC19. An EcoRI-BalI fragment homologous to the mouse muNTS1 (see, plant DNA sequence positions 1–446 shown in SEQ ID NO: 1) was then excised from Nt4-19 and ligated into the EcoRI and SmaI sites of the exemplary binary plant transformation vector pBin19, resulting in formation of plasmid pBin-aps.

Recombinant molecules for the expression of GFP were based on the plasmid pCK GFP S65C, a pUC derivative containing the mutated GFP DNA sequence under the control of the CaMV 35S promoter with two enhancers. Reichel et al., Proc. Natl. Acad. Sci. (USA) 93:5888–5893 (1996).

A GFP expression cassette derived from pCK GFP S65C and composed of the cauliflower mosaic virus 35S promoter with a duplication in the upstream regulatory sequence, the TEV 5' nontranslated sequence, the GFP sequence, and the cauliflower mosaic virus polyadenylation signal, was excised with HindIII and ligated into the dephosphorylated HindIII site of pBin-aps, creating pNB35S-GFP-aps1 and pNB35S-GFP-aps2. These two recombinant molecules differ from each other in the orientation of the expression cassette relative to the plant-active APS and NPTII (i.e., neomycin phosphotransferase coding region) elements. (See FIG. 2).

A control plasmid capable of expressing GFP from the CaMV 35S promoter, but lacking an APS, was constructed and designated pNB35S-GFP. This plasmid was generated by initially restricting pCK GFP S65C with HindIII, thereby excising a fragment containing the GFP coding region flanked, in proper orientation, by the CaMV 35S promoter (including two enhancer sequences and the TEV 5' nontranslated sequence) and a terminator sequence. The vector pBin19, containing the previously described NPII selectable marker, was digested with HindIII. The GFP-containing fragment from pCK GFP S65C was then inserted into pBin19, thereby generating pNB35S-GFP. (See FIG. 2).

EXAMPLE 2

The recombinant molecules described in Example 1 were separately introduced into tobacco plants using *Agrobacterium tumefaciens*. The streptomycin resistant Agrobacterium strain LBA4404, used for plant transformation, was itself transformed with the corresponding recombinant molecules using a variation of the freeze-thaw procedure described by Hood et al., J. Bacteriol. 168:1291–1301 (1986). The transformed Agrobacterium cells were prepared using a standard transformation protocol, followed by growth at 28° C. for 40–48 hours in liquid YM medium containing streptomycin and kanamycin, each at 50 mg/L. One liter of YM medium contains 0.4 g yeast extract (autolyzed, low sodium); 10 g mannitol, 0.1 g NaCl, 0.2 g $MgSO_4$ and 0.5 g of $K_2HPO_4$. YM medium (Gibco BRL) is specifically formulated for the growth and expression of Agrobacterium. Transformation of *Agrobacterium tumefaciens* LBA4404 was confirmed by Southern DNA hybridization. Although *Agrobacterium tumefaciens* LBA4404 and recombinant molecules derived from pBin19 are preferred for use in practicing the present invention, any of the conventionally known and available plant transformation vectors can be modified by introducing a plant-active APS sequence and used in conjunction with any suitable *Agrobacterium tumefaciens* strain in practicing the methods of the invention.

Transformation of tobacco plants (e.g., *Nicotiana tabacum* cv. Wisconsin and cv. Samsun NN) was effected by leaf-disk co-cultivation, as described by Weissbach et al., in Plant Molecular Biology-Technique (Academic Press, Inc. San Diego 1988). Healthy unblemished leaves were harvested from sterile young plants and cut into strips 5–10 mm wide. These explant tissues were infected by submersion in a suspension of transformed Agrobacterium cells. Following exposure to Agrobacterium, explant tissues were then blotted dry on sterile filter paper, inverted, placed on MS medium in tissue culture plates and incubated for a co-cultivation period of 36–48 hours. (MS medium is a conventional medium for the in vitro culture of plants, Murashige et al., Physiol. Plantarum 15:473–479 (1962)). Subsequently, explants were transferred to agar plates (8 g/L) containing regeneration medium (MS salts, 30 g/L sucrose, 1 mg/L BAP (i.e., 6-benzylaminopurine, a plant cytokinin), 500 mg/L of carbenicillin to eliminate bacterial growth, and 100 mg/L of kanamycin as a selective agent for transgenic plants). Transformants were selected on the same medium without any hormone. Incubation was continued until roots had formed.

EXAMPLE 3

Copy numbers of specific DNAs in transgenic tobacco plants were determined by Southern blot analyses. Total genomic DNA was independently isolated from five transgenic plants containing pNB35S-GFP-aps1, five transgenic plants containing pNB35S-aps2, and two transgenic plants containing pNB35S-GFP. DNA isolations were performed using the Phytopure plant DNA extraction kit from Nucleon Biosciences according to the manufacturer's instructions. Following isolations, genomic DNAs were digested to completion with HindIII and equal quantities were fractionated by agarose gel electrophoresis using standard techniques. Fractionated DNAs were then transferred to HyBond-$N^+$ membranes (Amersham Corp.) and exposed to a $^{32}P$-labeled probe specific for the GFP coding region using a Southern hybridization protocol known in the art. Sambrook et al. (1989). Results were visualized using a Phospho-Imager SI System (Molecular Dynamics, Inc.) and the data were evaluated using proprietary Phospho-imager software. The results showed a 3–15 fold amplification of the GFP coding region when adjacent to the APS, relative to the GFP coding region levels in the absence of an adjacent APS.

Production of specific mRNA levels in the transgenic tobacco plants was also determined. Northern blot analyses were performed using total RNA isolated from leaf tissues in accordance with the procedure of Chomczynski et al., Anal. Biochem. 162:156–159 (1987). 10 $\mu$g of isolated RNA were separated by denaturing 1.5% agarose gel electrophoresis, transferred onto Hybond $N^+$ membrane (Amersham Inc., Arlington Heights, Ill.) and hybridized to a $^{32}P$-dCTP labeled DNA fragment encoding GFP. The DNA fragment used as a hybridization probe was prepared by digestion of pCK-GFP-C65 with NcoI and XhaI followed by agarose gel fractionation and isolation of the DNA fragment encoding GFP. Hybridization was performed overnight at 65° C. according to the protocol of Church et al., Proc. Natl. Acad. Sci. (USA) 81:1991–1995 (1985), using HYPE buffer (1% BSA, 1 mM EDTA, 0.5M $Na.PO_4$ pH 7.2, 7% SDS) as a hybridization buffer. After hybridization, filters were washed twice for 5 minutes at 65° C. in wash buffer 1 (0.5% BSA, 1 mM EDTA, 0.04 M $NaHPO_4$ pH 7.2, 5% SDS), followed by four washes for 5 minutes each at 65° C. in wash buffer 2 (1 mM EDTA, 0.04 M $NaHPO_4$ pH 7.2, 1% SDS). Radioactive hybridization signals were detected with the Phospho-Imager SI System. Relative expression levels of GFP mRNA were quantified using the ImageQuanNT image analysis software package available from Molecular Dynamics, Inc. The quantification data showed a 2 to 20 fold stimulation of heterologous mRNA expression in transgenic plants containing the amplification promoting sequence from transformation plasmids pNB35S-GFP-aps1 and pNB35S-GFP-aps2, as compared to transgenic tobacco transformed with pNB35S-GFP. The relative increases of 2 to 20 fold in mRNA production may not be due solely to the copy number effect which resulted in a 3 to 15 fold amplification of specific DNAs.

The effect of an APS sequence on expression was also revealed by plating transformants on selective MS medium containing increasing concentrations of kanamycin and determining the frequency of surviving colonies. Cells from plants transformed with either of the APS-containing plasmids had enhanced survival characteristics, attributable to increased expression of the NPTII gene. These results indicate that an amplification of the NPTII gene had also occurred.

To show that the elevated mRNA levels in APS transformed plants were correlated with an increased synthesis of recombinant protein, GFP expression was measured using both fluorescent and immunological techniques. The unique bioluminescent features of GFP (excitation at 475 nm; emission at 510 nm) were used to microscopically detect this protein in plant tissues. Plant roots, freshly prepared in 0.05 M Tris HCI pH 8.0, were irradiated in the long-UV range of the electromagnetic spectrum with a fluorescent microscope (Nikon, Inc) for an empirically optimized period of 30 seconds. Qualitative measurements showed that the roots of transgenic plants containing pNB35S-GFP-aps1 or pNB35S-GFP-aps2 fluoresced brightly, in contrast to the roots of transgenic plants containing the control plasmid pNB35-GFP, which did not fluoresce.

For Western blot analysis, GFP was detected using anti-GFP monoclonal antibodies produced by mouse hybridoma cells (Clontech, Inc.) using the Western Exposure Chemiluminescent Detection System PT 1 600-1, available from the same supplier. Proteins extracted from the leaves were separated on 12% SDS-PAGE and electrophoretically transferred onto PVDF membranes using the Bio-Rad Mini-Protein system (100 V constant voltage at 4° C., 1.5 hours). Pre-stained low-molecular weight SDS-PAGE standards (Bio-Rad Laboratories, Inc.) were used as molecular weight markers. Primary antibodies were diluted 1:500 and the secondary antibody—phosphatase conjugate was diluted 1:15,000. A single sharp protien band corresponding to the expected size of 27 kDa was detected.

The quantification of recombinant protein in leaf extracts was also performed by indirect enzyme-linked immunosorbent assay (ELISA) using polyclonal antibodies to GFP as primary antibodies and horseradish peroxidase (EC.1.11.1.7) labeled antibodies as secondary antibodies. ABTS (2,2'-azino-bis (3-ethylbenzthiazoline)-6-sulfonic acid) was used as substrate for the peroxidase in the colorimetric detection reaction. Optical density was determined spectrophotometrically at 405 nm using a PERKIN-ELMER Spectrofluorimeter LF-50B. The ELISA data showed 3 to 30 times higher amounts of GFP expressed from pNB35S-GFP-aps1 and pNB35S-GFP-aps2 plants as compared to the GFP expression levels in pNB35SGFP plants. These results establish a positive correlation between GFP mRNA levels and GFP protein levels in transgenic plants expressing heterologous genes adjacent to an APS.

The preceding illustrative examples provide presently preferred embodiments of the invention which are clearly non-limiting on practice of the invention.

Thus, while the illustrative examples employ an APS comprising 446 nucleotides which is an exact replica of a sequence within an rDNA intergenic region of *N. tabacum*, the invention is not limited to use of such a sequence. Novel isolated APS polynucleotides may also be derived from other plant species, especially those wherein rDNA intergenic regions are revealed as including A-T rich sequences. As noted in Borisjuk et al. (1997), similar A-T rich regions are found in *L. esculentum, S. tuberosum* and several other plants and are expected to be equally suitable for practice of the invention. Moreover, by analogy to development of "consensus" expression regulatory sequences based on regulatory sequences of multiple protein genes, it is expected that synthetic "consensus" plant APSs can be developed based on the A-T rich rDNA intergenic regions of several different plants.

Moreover, novel transformation methods and transformed plant cells and plants of the invention are not limited to incorporation of APSs derived from (or predominantly based on) plants and can involve use of "plant active" APSs derived from non-plant sources. The substantial sequence homology between a portion of the *N. tabacum* rDNA intergenic sequence and a portion of mouse muNTS1 sequence revealed in FIG. 1 indicates that all or part of the 370 base pair muNTS 1 mouse APS, and other eukaryotic APS sequences, can be active to amplify adjacent target sequences in plants.

While exemplary APS according to the invention has the 446 base sequence set forth in SEQ ID NO: 1, plant functional APSs are expected to exhibit a range of lengths. For example, Wegner et al., (1989) disclosed a length of 370 bp for muNTS1 along with a series of fragments ranging from 56 to 1,200 bp that contained an active muNTS 1. Given the functional (i.e., amplification promotion) characteristic of an APS according to the invention, determination of a minimum, maximum and/or optimum APS length is within the skill in the art, involving no more than routine optimization of a known parameter. For example, the skilled artisan can readily synthesize fragments or generate terminal deletions of cloned sequences in a processive manner to localize a sequence having APS activity; similarly, one of ordinary skill could create point or cluster polymorphisms to determine the need for internal nucleotides in an APS sequence capable of promoting amplification.

The invention thus comprehends novel isolated plant APSs having a sequence that hybridizes under stringent conditions to an APS having the complement of the sequence set forth in SEQ ID NO: 1. Exemplary stringent hybridization conditions include hybridization at 65° C. in 3×SSC, 20 mM $NaPO_4$ (pH 6.8) and washing at 65° C. in 0.2×SSC. It is understood by those of skill in the art that variation in these conditions occurs based on the length and GC base content of the sequences to be hybridized. Formulas standard in the art are appropriate for determining exact hybridization conditions. See Sambrook et al., §§9.47–9.51 (1989).

A target nucleic acid may comprise a protein coding region (such as the GFP and NPII sequences exemplified above) or a regulatory domain. These target nucleic acids also may be homologous or heterologous to host nucleic acids depending on the plant host cell. The suitability of a given target nucleic acid length is readily determinable by assessing whether an APS is capable of amplifying that target nucleic acid, using the disclosures provided herein. Such assessments are routine for those of ordinary skill in the art.

To amplify a target nucleic acid, a polynucleotide specifying an APS is placed adjacent to the target nucleic acid, i.e., located on the same nucleic acid molecule as the target. Thus, "adjacent" as used herein does not mean that the APS and the target nucleic acid must exhibit a direct physical connection or requisite 3' or 5' orientation. In analogous constructs, for example, entire vectors containing, e.g., a muNTS1 sequence have been amplified in mammalian cells, indicating that a separation of several kb does not prevent a mammalian APS from amplifying a target nucleotide sequence. Hemann et al. (1994). Although several kb may separate an APS from a target, it is preferred that the APS be found within 3 kb of the target nucleic acid. Again, suitable maximum or optimum separations between an APS and a target nucleic acid may be determined by the skilled artisan using conventional techniques in routine experiments. It is generally expected that the closer an APS and a target nucleic acid are located, the greater the likelihood that the APS will be active in promoting the amplification of the target.

Amplification of the target nucleic acid is designed to affect the physiology of the host cell in a desirable way. For example, a target nucleic acid comprising a regulatory signal may provide a binding site for a regulatory polypeptide. Amplification of the binding site would titrate out the regulator, thereby altering the expression of the regulated genes, such as genes encoding commercially valuable gene products. Alternatively, the target nucleic acid may itself encode a valuable gene product such as a polypeptide useful in medical diagnostics or therapeutics.

The invention also contemplates nucleotide segments wherein an APS placed adjacent to at least one (flanking) homologous recombination locator nucleotide sequence that is similar to a region adjacent a target nucleic acid sequence with a level of similarity sufficient to allow for insertional homologous recombination to occur close enough to permit the APS to promote the amplification of the target.

Vectors according to the invention may contain any of the foregoing nucleic acid molecules or constructs. Suitable vectors include plasmid, viral, and plasmid/viral (e.g., phagemid) hybrid vectors, as well as unmodified chromosomes and modified chromosomal vectors such as YACs. These vectors facilitate the stable introduction of at least one APS into a host plant cell. The vectors may also contain expression control elements such as promoters, enhancers, or sequences that facilitate translation initiation, as would be understood in the art.

Host cells according to the invention may be derived from a wide variety of sexually or vegetatively propagated plants, as well as intact living plant portions such as excised leaves, stems, roots, flowers, and tissues. Preferred for use in the methods of the invention are the cells of plant species representing different plant families such as tobacco (e.g., *N. tabacum*), tomato (e.g., *L. esculentum*), potato (e.g., *S. tuberosum*), and weeds (e.g., *A. thaliana*; see Grundler et al., J. Mol. Biol. 221:1209–1221 (1991)). In addition to these and other dicot exemplars, the invention contemplates monocot plants such as the grasses. Further, a plant of the present invention may be a mature plant or an immature plant such as a seedling. Preferred plants are capable of being sustained without organic nutrient supplementation and do not require sterile conditions.

Another aspect of the invention is directed to methods for amplifying a target nucleic acid within plant cells. The methods include a step for contacting a polynucleotide specifying an APS with a plant host cell. Following the contacting step, the methods according to the invention require minimal operator intervention. In some embodiments, the introduced nucleic acid molecules will affect host cell physiology without additional intervention. In other embodiments, the introduced nucleic acid molecules affect the copy number of a target nucleic acid, with either a direct or indirect effect on the expression of an encoded polypeptide. In these embodiments, the produced polypeptide may be recovered, using conventional cell culture and protein recovery techniques. Alternatively, the plant host cells may be subjected to regeneration protocols to produce intact plants expressing the polypeptide of interest. These plants may then be subjected to invasive or non-invasive recovery techniques known in the art.

Beyond the traditional use of Agrobacterium-based transformation protocols to transform dicots (see Example 2), it has been shown that Agrobacterium-based methods may also be employed to transfer heterologous (i.e., non-native) nucleic acids to monocot species in the generation of transgenic plants for use in methods according to the invention. Vain et al., Biotech. Advances 13:653–671 (1995), incorporated herein by reference.

Other transformation methodologies may also be employed to generate transgenic plants. For example, direct DNA transfer into plant cell protoplasts may be effected by the conventional techniques of calcium phosphate co-precipitation, the use of poly-L-ornithine, liposome-mediated transformation, electroporation, microinjection or fusagen-mediated (e.g., polyethylene glycol) transformation, and plants regenerated from the transformed protoplasts. PCT/US84/00050 and Christou, Euphytica 85: 13–27(1995), each incorporated herein by reference. Other transfer methodologies such as biolistic transformation (i.e., microprojectile or particle bombardment) do not require plant cell protoplasts, thereby simplifying the process of regenerating transgenic plants. Consequently, biolistic transformation may be employed to introduce the coding region of a heterologous polypeptide, operatively linked to an APS, into a wide variety of plants, including both monocots and dicots. Christou (1995); Jahne et al., Euphytica 85:35–44 (1995), incorporated herein by reference.

Regeneration of transgenic plants from transformed cells, including transformed protoplasts, may be accomplished using any one of several techniques known in the art. Several approaches to the regeneration of transgenic plants are disclosed in EP-A-0 243 553, incorporated herein by reference. These approaches include regeneration via embryogenic or organogenic routes. Alternatively, plants may be regenerated following transformation by a method that incorporates a step for inducing meristem reorganization to increase the probability of obtaining transgenic germ cells, followed by a step providing conditions promoting differentiation of the meristem. PCT/US95/08977, incorporated herein by reference. In general, any of the transformation and regeneration methodologies known in the art may be used to generate transgenic plants for use in methods according to the invention. Alternatively, plant host cells transformed with a polynucleotide according to the invention may be maintained in culture using conventional techniques, rather than subjecting such cells to regeneration regimens to generate transgenic plants. Regenerated transgenic plants then may be subjected to conventional nucleic acid and/or polypeptide recovery techniques in accordance with methods of the invention.

While the present invention has been described in terms of specific embodiments, it is understood that variations and modifications will occur to those skilled in the art. Accordingly, only such limitations as appear in the appended claims should be placed upon the invention.

What is claimed is:

1. A method for amplifying a target nucleic acid comprising the step of contacting a plant host cell under conditions suitable for transforming or transfecting said cell with an isolated polynucleotide specifying a plant-active Amplification Promoting Sequence (APS), said polynucleotide selected from the group consisting of:

a) a polynucleotide comprising the sequence set forth in SEQ ID NO:1; and b) a polynucleotide which hybridizes to a polynucleotide having the complement of the sequence set forth in step a), said hybridization occurring in 3×SSC, 20 mM $NaPO_4$ (pH 6.8) at 65° C. with washing in 0.2×SSC at 65° C.

2. The method according to claim 1 wherein said isolated polynucleotide further comprises a target nucleic acid.

3. The method according to claim 2 wherein the target nucleic acid comprises a coding region.

4. The method according to claim 3 further comprising the step of recovering the expression product of said target nucleic acid.

5. The method according to claim 1 wherein said isolated polynucleotide further comprises a homologous recombination locator polynucleotide.

6. An isolated polynucleotide segment specifying an Amplification Promoting Sequence (APS) that is active in plants to amplify a target nucleic acid, said segment comprising an APS comprising:

a) a polynucleotide comprising the sequence set forth in SEQ ID NO:1; or b) a plant-derived polynucleotide which hybridizes to a polynucleotide having the complement of the sequence set forth in step a), said hybridization occurring in 3×SSC, 20 mM $NaPO_4$ (pH 6.8) at 65° C. with washing in 0.2×SSC at 65° C.; and said segment further comprising c) an animal or non-rDNA plant target nucleic acid; or d) an animal or non-rDNA plant homologous recombination locator polynucleotide.

7. The polynucleotide segment according to claim 6, wherein said plant-active APS comprises an rDNA intergenic sequence.

8. The polynucleotide segment according to claim 7 wherein said rDNA intergenic sequence is derived from a plant selected from the group consisting of *N. tabacum, L. esculentum* and *S. tuberosum.*

9. The polynucleotide segment according to claim 8 wherein said APS is within about 3,000 nucleotides of said target nucleic acid.

10. An expression cassette comprising the polynucleotide segment according to claim 6.

11. A vector comprising the polynucleotide segment according to claim 6.

12. A plant host cell transformed or transfected with the polynucleotide segment according to claim 6.

13. An isolated polynucleotide consisting of the sequence set forth in SEQ ID NO:1.

14. An isolated polynucleotide consisting of the sequence set forth at nucleotide 102 to nucleotide 161 of SEQ ID NO:1.

* * * * *

SEQUENCE LISTING

```
(1) GENERAL INFORMATION:

   (iii) NUMBER OF SEQUENCES: 1


(2) INFORMATION FOR SEQ ID NO:1:

     (i) SEQUENCE CHARACTERISTICS:
          (A) LENGTH: 446 base pairs
          (B) TYPE: nucleic acid
```

-continued

```
        (C) STRANDEDNESS: single
        (D) TOPOLOGY: linear

   (ii) MOLECULE TYPE: other nucleic acid
        (A) DESCRIPTION: /desc = "APS rDNA sequence"

   (xi) SEQUENCE DESCRIPTION: SEQ ID NO:1:

GATATCGGAA TCACTTATGG TGGTTGTCAC AATGGAGGTG CGTCATGGTT ATTGGTGGTT     60

GGTCATCTAT ATATTTTTAT AATAATATTA AGTATTTTAC CTATTTTTTA CATATTTTTT    120

ATTAAATTTT ATGCATTGTT TGTATTTTTA AATAGTTTTT ATCGTACTTG TTTTATAAAA    180

TATTTATTAT TTTATGTGTT ATATTATTAC TTGATGTATT GGAAATTTTC TCCATTGTTT    240

TTTCTATATT TATAATAATT TTCTTATTTT TTTGTATTTT ATTATGTATT TTTTCGTTTT    300

ATAATAAATA TTTATTAAAA AAAATATTAT TTTTTGTAAA ATATATCATT TACAATGTTT    360

AAAAGTCATT TGTGAATATA TTAGCTAAGT TGTACTTCGG TTTGTGCATT TTGGTGTTGT    420

ACATGTCTAT TATGATTCTC TGGCCA                                         446
```